(12) United States Patent
Wang et al.

(10) Patent No.: US 9,463,461 B2
(45) Date of Patent: Oct. 11, 2016

(54) SELF-CONTAINED CARTRIDGE AND METHODS FOR INTEGRATED BIOCHEMICAL ASSAY AT THE POINT-OF-CARE

(71) Applicant: The Johns Hopkins University, Baltimore, MD (US)

(72) Inventors: Tza-Huei Wang, Timonium, MD (US); Dong Jin Shin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/523,412

(22) Filed: Oct. 24, 2014

(65) Prior Publication Data
US 2015/0118740 A1 Apr. 30, 2015

Related U.S. Application Data

(60) Provisional application No. 61/895,739, filed on Oct. 25, 2013.

(51) Int. Cl.
*B01L 3/00* (2006.01)
*B01L 7/00* (2006.01)
(Continued)

(52) U.S. Cl.
CPC ...... *B01L 3/502761* (2013.01); *B01L 3/50273* (2013.01); *B01L 7/52* (2013.01); *B01L 2200/04* (2013.01); *B01L 2200/0647* (2013.01); *B01L 2200/0673* (2013.01); *B01L 2200/12* (2013.01);
(Continued)

(58) Field of Classification Search
CPC ............ B01L 3/502784; B01L 3/502761; B01L 3/502707; B01L 2300/887; B01L 2300/161; B01L 2300/0858; B01L 2200/0673; B01L 2200/0647; B01L 2400/043; G01N 33/50; G01N 35/0098
See application file for complete search history.

(56) References Cited

U.S. PATENT DOCUMENTS 5,200,152 A * 4/1993 Brown ................... B01L 3/5027
356/244
6,485,690 B1 * 11/2002 Pfost .................... B01J 19/0046
422/552
(Continued)

FOREIGN PATENT DOCUMENTS

WO 2006071770 A2 † 6/2006

OTHER PUBLICATIONS

Masek et al., "Performance of Three Nucleic Acid Amplification Tests for Detection of Chlamydia trachomatis and Neisseria gonorrhoeae by Use of Self-Collected Vaginal Swabs Obtained via an Internet-Based Screening Program", Journal of Clinical Microbiology, vol. 47, No. 6, Jun. 2009, pp. 1663-1667.
(Continued)

*Primary Examiner* — Brian R Gordon
(74) *Attorney, Agent, or Firm* — MH2 Technology Law Group, LLP

(57) ABSTRACT

Provided is a sample processing cartridge. The sample processing cartridge can include a housing and a channel disposed in the housing. The housing can include a sample inlet for receiving at least one biological sample. The channel can in fluidic communication with the sample inlet and can be defined by an upper surface and a lower surface. The upper surface can include a hydrophilic portion and a hydrophobic portion. The lower surface can include a hydrophilic portion and a hydrophobic portion. The hydrophilic and hydrophobic portions of the upper and lower surfaces of the channel can be configured to isolate at least one aqueous reagent.

9 Claims, 8 Drawing Sheets

(51) Int. Cl.
*G01N 33/50* (2006.01)
*G01N 35/00* (2006.01)

(52) U.S. Cl.
CPC . *B01L 2300/0858* (2013.01); *B01L 2300/0887* (2013.01); *B01L 2300/161* (2013.01); *B01L 2400/043* (2013.01); *G01N 33/50* (2013.01); *G01N 35/0098* (2013.01)

(56) References Cited

U.S. PATENT DOCUMENTS

| | | | | |
|---|---|---|---|---|
| 6,555,389 B1 * | 4/2003 | Ullman | ............... | B01L 3/5025 422/502 |
| 6,565,813 B1 * | 5/2003 | Garyantes | ............ | B01F 13/0071 422/553 |
| 7,998,436 B2 * | 8/2011 | Pollack | ............... | C07K 1/1136 422/500 |
| 8,093,064 B2 | 1/2012 | Shah et al. | | |
| 8,216,855 B2 | 7/2012 | Pipper et al. | | |
| 8,327,726 B2 * | 12/2012 | Kim | ................... | B01L 3/50273 422/402 |
| 8,372,658 B2 | 2/2013 | Shikida et al. | | |
| 8,440,150 B2 | 5/2013 | Den Dulk et al. | | |
| 8,491,840 B2 * | 7/2013 | Cho | ................... | B01F 11/0002 422/502 |
| 8,539,823 B2 * | 9/2013 | Lee | ................ | G01N 35/00029 137/803 |
| 8,628,972 B2 * | 1/2014 | Tang | ............... | G01N 33/56905 422/502 |
| 8,685,344 B2 * | 4/2014 | Sudarsan | ............ | B01F 13/0071 204/600 |
| 8,758,682 B2 | 6/2014 | Axen et al. | | |
| 8,821,705 B2 * | 9/2014 | Bjornson | ......... | B01L 3/502715 204/450 |
| 2004/0037739 A1 * | 2/2004 | McNeely | ................. | B01F 5/10 422/417 |
| 2004/0208792 A1 * | 10/2004 | Linton | ................. | B01L 3/5025 422/552 |
| 2008/0213853 A1 | 9/2008 | Garcia et al. | | |
| 2009/0246782 A1 † | 10/2009 | Kelso | | |
| 2010/0273142 A1 | 10/2010 | Prins et al. | | |
| 2011/0212509 A1 † | 9/2011 | Beebe | | |
| 2012/0004139 A1 * | 1/2012 | Staker | .................. | B01L 3/5027 506/16 |
| 2012/0063972 A1 * | 3/2012 | Brown | ................. | B01L 3/5027 422/502 |
| 2012/0129156 A1 | 5/2012 | Kelso et al. | | |
| 2013/0043150 A1 | 2/2013 | Ohashi | | |
| 2014/0322103 A1 * | 10/2014 | McDevitt | ............. | B01L 3/5025 422/554 |

OTHER PUBLICATIONS

Notomi et al., "Loop-mediated isothermal amplification of DNA", Nucleic Acids Research, vol. 28, No. 12, 2000, pp. 1-7.

Zhang et al., "A surface topography assisted droplet manipulation platform for biomarker detection and pathogen identification", The Royal Society of Chemistry, Lab Chip, 11, 2011, pp. 398-406.

\* cited by examiner
† cited by third party

SELF-CONTAINED CARTRIDGE AND METHODS FOR INTEGRATED BIOCHEMICAL ASSAY AT THE POINT-OF-CARE

RELATED APPLICATIONS

This application claims priority from U.S. Provisional Patent Application Ser. No. 61/895,739 filed on Oct. 25, 2013, the contents of which are incorporated by reference herein in its entirety.

GOVERNMENT SUPPORT STATEMENT

This invention was made with government support under Grant Nos. R01CA155305, U54CA151838, R21CA173390 awarded by the National Institutes of Health, and under Grant Nos. 1159771, 0967375 awarded by the National Science Foundation. The government has certain rights in the invention.

FIELD OF THE INVENTION

This invention relates generally to the field of biochemical reactors, particularly biochemical assay platforms for nucleic acid testing of infectious agents in biological samples, specifically for the detection of *Chlamdydia trachomatis* (Ct).

BACKGROUND OF THE INVENTION

Biochemical reactors such as assay platforms for detecting infectious agents such as venereal diseases are known in the art. In such devices, samples are collected and processed to extract nucleic acids according to a multi-step process. Generally, the multi-step process involves removing excess components or non-desired components from the biological sample, filtering and concentrating the sample, washing the remaining filtered and concentrated sample and providing it to an analysis chamber where it may be exposed to a reaction mixture which allows for the identification of the agent, such as an infectious agent, of interest. However, because isolating the infectious agents is complicated, many conventional platforms require a skilled end user to perform multiple fluidic handling steps after loading the sample. For example, the APTIMA COMBO 2® (available from Gen-Probe, Inc. San Diego, Calif.), which some consider the gold standard for detecting Ct, suffers from limitations, such as requiring multiple fluidic handling steps to process a sample.

Accordingly, what is needed in the art is an assay platform that minimizes the number of fluidic handling steps that an end user must perform, thereby increasing isolation efficiency and reducing erroneous results.

SUMMARY

In an embodiment, there is a sample processing cartridge that includes an upper cartridge portion, a lower cartridge portion and a spacer frame disposed between the cartridge portion. The upper cartridge portion can include a first hydrophobic layer disposed on a first substrate, and the lower cartridge portion can include a second hydrophobic layer disposed on a second substrate. A channel that is at least partially defined by sidewalls of the spacer frame, and fluidically couples a sample inlet section and a sample analysis section of the cartridge, can be at least partially filled with an isolation medium. At least one magnetic bead can be disposed in the channel and is capable of being transported through the isolation medium and from the inlet section to the sample analysis section via, for example, an external magnetic force. At least one aqueous reagent can be disposed in the channel. At least one aqueous reagent can be disposed in the channel and may be isolated by the isolation medium. A portion of the at least one aqueous reagent pendant contacts one of the plurality of exposed hydrophilic surfaces of the first substrate. At least one biochemical reaction mixture can be disposed in the analysis section of the cartridge and may be isolated by a isolation medium. A portion of the at least one biochemical reaction mixture may contact another one of the plurality of exposed hydrophilic surfaces of the first substrate. Another portion of the at least one biochemical reaction mixture may contact the exposed hydrophilic surface of the second substrate.

In yet another embodiment, there is a method of making a sample processing cartridge. The method can include providing an upper cartridge portion by forming a first hydrophobic layer on a first substrate, providing a lower cartridge portion by forming a second hydrophobic layer on a second substrate and providing a spacer portion which can be formed between the upper portion and the lower portion. The method can further include forming a channel that is at least partially defined by sidewalls of a spacer frame formed by patterning the spacer portion. The channel can fluidically couple a sample inlet section and a sample analysis section. The method can further include at least partially filling the channel with an isolating medium. The method can further include providing at least one magnetic bead disposed in the channel, forming a plurality of first openings that extend through the first hydrophobic layer to expose a corresponding plurality of surface portion of the first substrate, and forming at least one second opening that extends through the second hydrophobic layer to expose a corresponding surface portion of the second substrate to the channel. The method can also include providing at least one aqueous reagent pendant to the channel, wherein a portion of the at least one aqueous reagent pendant contacts one of the plurality of exposed hydrophilic surface of the first substrate, and another portion of the at least one aqueous reagent contacts one of the hydrophobic surfaces exposed by the at least one second opening of the second hydrophobic layer. The method can also include providing at least one biochemical reaction mixture to the analysis section, wherein a portion of the at least one biochemical reaction mixture contacts another one of the exposed surface portions of the first substrate, and another portion of the at least one biochemical reaction mixture contacts the exposed surface of the second substrate.

In even still another embodiment, there is an automated sample processing system. The system can include a sample processing cartridge, a manipulator comprising an actuator, an arm connected to the actuator and a magnet connected to the arm and an automation host device for controlling the manipulator, the automation host device configured to provide data transmission to a controller in communication with the actuator for manipulating the arm such that the magnet is brought within a predetermined distance to the cartridge. The sample processing cartridge can include a housing and a channel disposed in the housing. The housing can include a sample inlet for receiving at least one biological sample. The channel can in fluidic communication with the sample inlet and can be defined by an upper surface and a lower surface. The upper surface can include a hydrophilic portion and a hydrophobic portion. The lower surface can include a hydrophilic portion and a hydrophobic portion. The hydrophilic and hydrophobic portions of the upper and lower surfaces of the channel can be configured to isolate at least one aqueous reagent.

Advantages of at least one embodiment include the ability for an end user to perform only a single loading operation of a biological sample lysate and/or reduced hands-on time to assay due to automation and preloaded reagents.

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

DESCRIPTION OF THE EMBODIMENTS

Figure 1A:
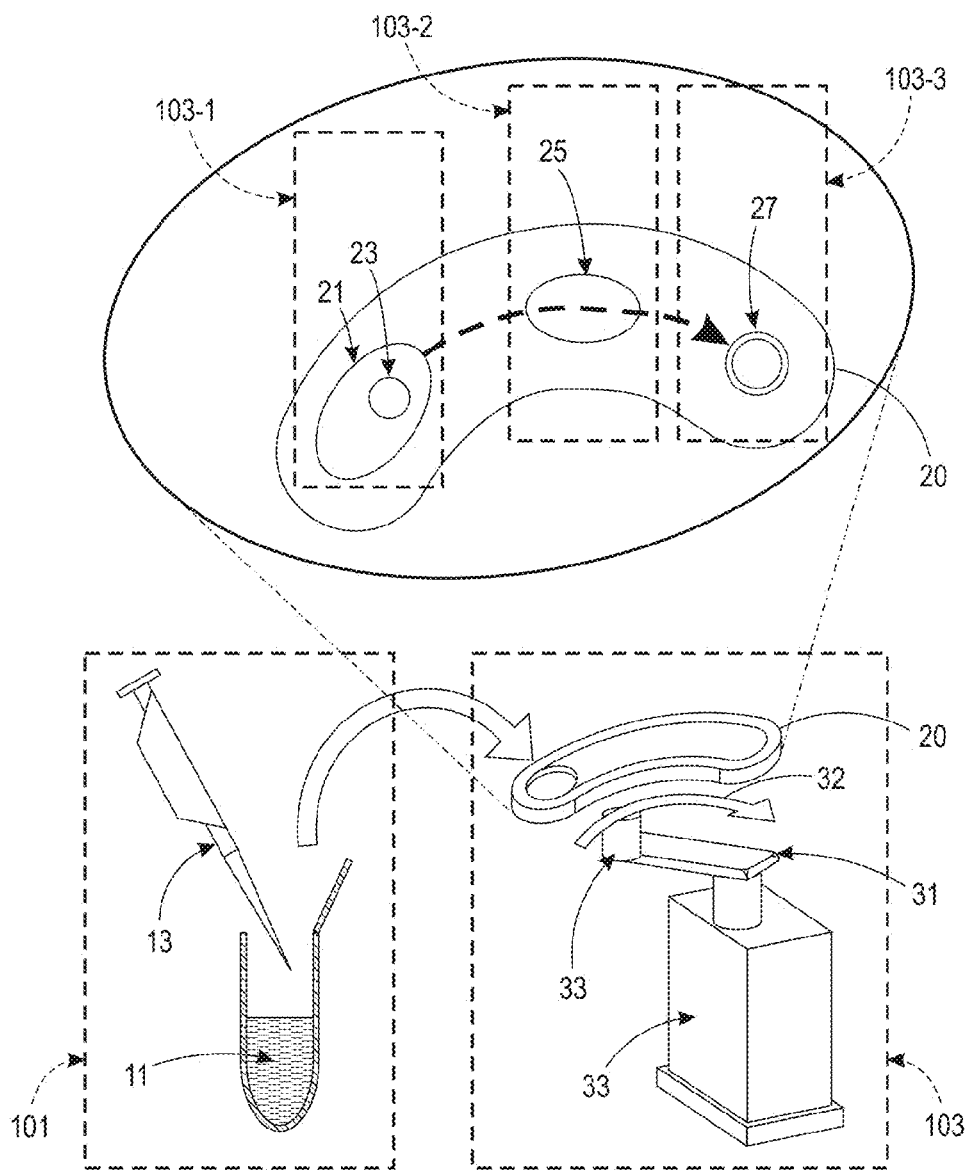
FIG. 1A illustrates an essay platform of an embodiment.

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the Figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Described herein are embodiments, such as an integrated nucleic acid amplification platform. For example, a self contained, miniaturized biochemical assay platform for nucleic acids testing of infectious agents from biological fluids. The platform can include a sealed plastic cartridge with patterned surfaces for reagent storage and fluidic processing. Biochemical reactions including nucleic acid amplification tests can be performed with a colorimetric readout.

Device actuation can be automated by a USB controlled servo motor compatible with control via laptop or handheld devices. In an embodiment, the fabrication and assembly process is performed for plastic cartridges. In an embodiment, a process based on a workflow for single stream colorimetric nucleic acid amplification assay is included. In an embodiment, the integrated nucleic amplification platform can be used for detection of *Chlamydia trachomatis* (Ct) infections from, for example, self-collected vaginal swab samples. The assay of such a platform can combine magnetic bead-based DNA purification with loop-mediated isothermal amplification (LAMP) to enable high-sensitivity nucleic acids testing with low-complexity instrumentation. The reagents can be processed on a droplet cartridge utilizing a novel lamination-based fabrication technique. The platform can utilize a simple rotary mechanism for a completely USB-powered actuation of magnetic beads.

In an embodiment there is an integrated and self contained device for sample processing, amplification and visual (colorimetric) detection of nucleic acid targets. Reagents can be internally contained on the device such that the end user only needs to perform a single loading operation of the sample lysate.

For example, FIG. 1A is an schematic flow-chart illustrating a method of processing an assay using an assay platform of an embodiment. As shown at 101, sample lysate 11 is loaded, for example, using a syringe 13, directly to an input chamber, such as through sample loading slot (not visible in FIG. 1A), of a cartridge 20 at 103.

Figure 2A:
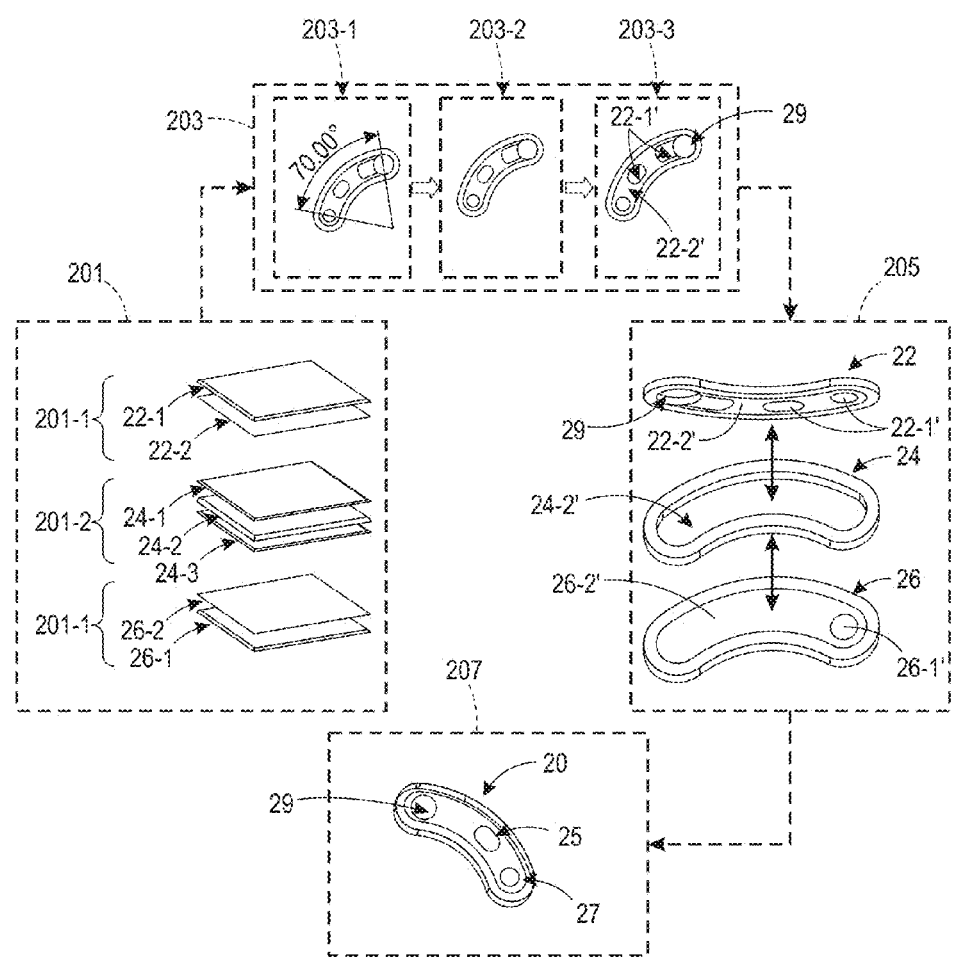
FIG. 2A illustrates a cartridge fabrication process of an embodiment.
Figure 2B:
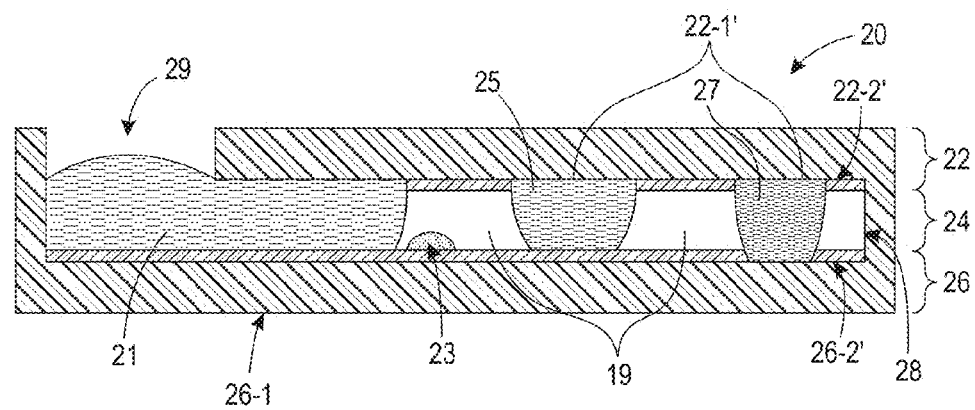
FIG. 2B is a side profile view of the cartridge at the end of the assembly of FIG. 2A.

As illustrated in FIG. 2A-2B and described further below, the cartridge 20 can be formed from an upper cartridge portion 22, a spacer portion 24 and a lower cartridge portion 26 each of which may be comprise any material, such as a polymer, for example PMMA, and which may each be formed as shown in FIG. 2A. Upon assembling each of upper section 22, center section 24 and bottom section 26 together, via, for example lamination, cartridge 20 can include a sample inlet 29 as an opening through which fluids and some solids can be provided into a channel 28 of the cartridge. For example, the cartridge may include a mixture of binding buffer 21 with paramagnetic beads 23, a wash buffer 25, and a LAMP reagent mixture 27, all of which may be disposed in a volume 28. Channel 28 may provide a conduit through which material may be transferred between a first stage 103-1, second stage 103-2 and third stage 103-3 of the cartridge 20.

Figure 5A:
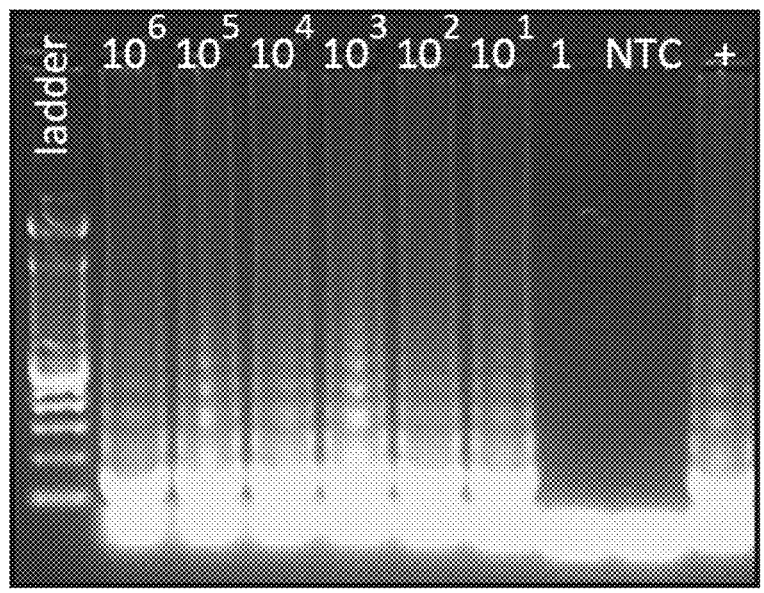
FIG. 5A shows sensitivity results obtained with *Chlamydia trachomatis* cell culture dilutions as sample verified using 2% agarose gel electrophoresis.
Figure 5B:
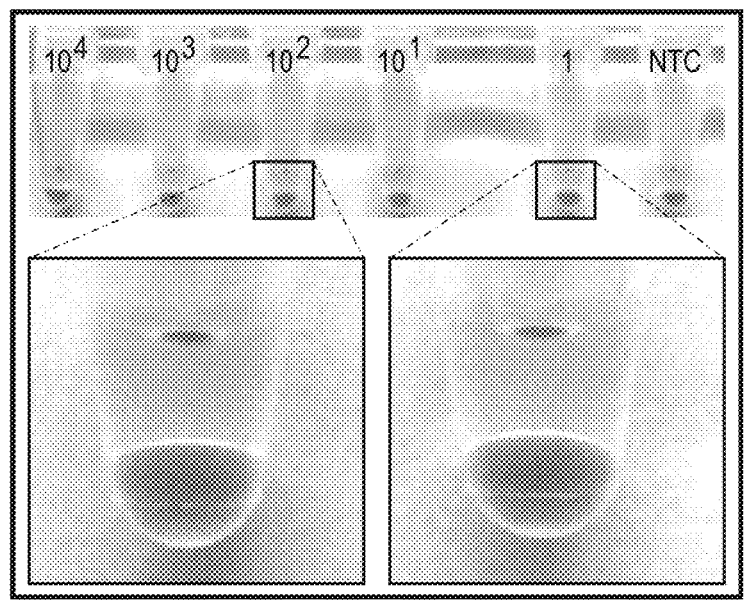
FIG. 5B shows sensitivity results for colorimetric readout of a processed sample.

Returning to FIGS. 1A-1B, in an embodiment, cartridge 20, which may be an automated DNA processing cartridge of an assay platform that includes an automation instrument 30, can accept a volume, such as 100 µL, of a material, such as a sample lysate 11 and can produce a calorimetric result, as shown in FIG. 5B. The calorimetric result can be attained within a time, such as within 1 hour, of introducing the sample 11 into the cartridge, extracting biological material of interest from the sample, and analyzing the biological material via calorimetric analysis. Generally, the biological material of interest can be separated from the sample by adhering the biological material it to the surface of, for example, the magnetic beads 23. The magnetic beads 23 can then be transported within, for example, cartridge 20, and passed through various materials, such as a binding buffer, isolation material, wash buffer, and more isolation material all while the biological material of interest is adhered to the surface of the magnetic beads. Finally, magnetic beads with biological material of interest adhered to the surface thereof may be moved into a LAMP reagent wherein the biological material may be separated from the surface of the beads. The biological material may then be incubated and allowed to react with components of the LAMP wherein analysis can be performed.

Figure 1B:
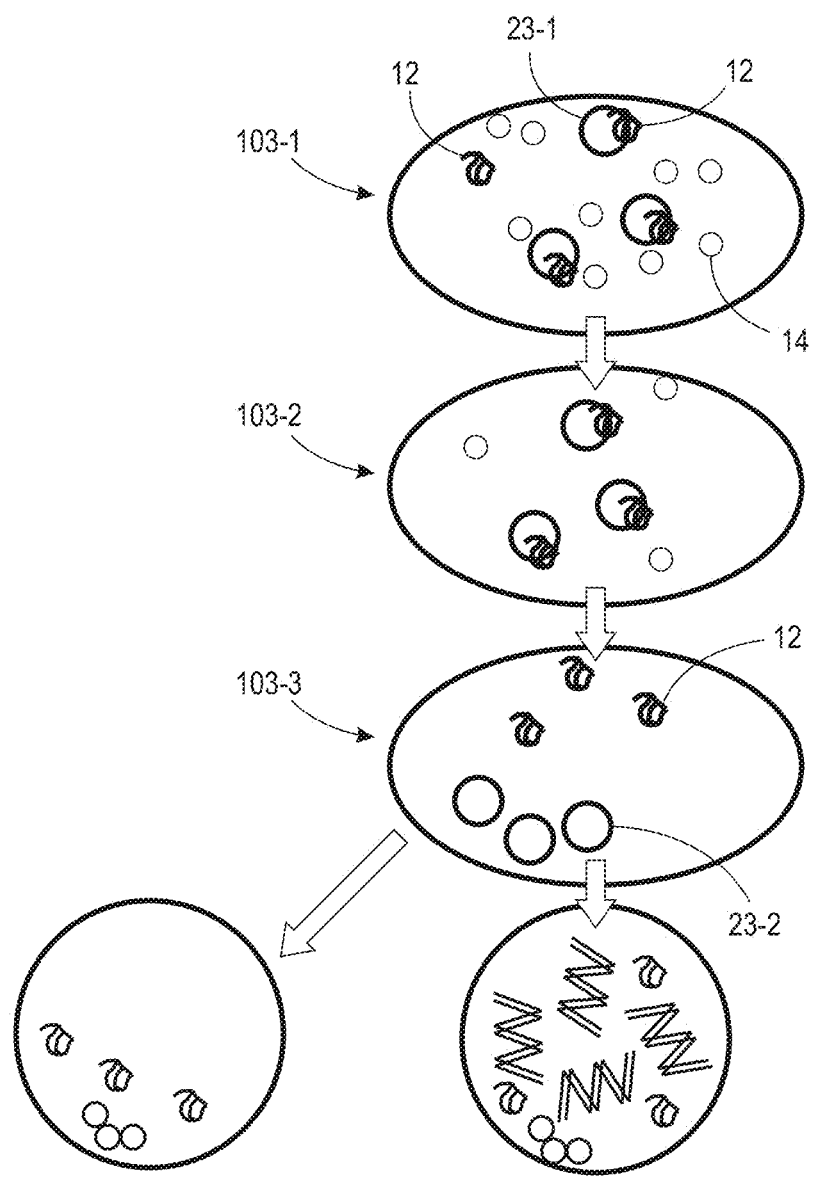
FIG. 1B provides an overview/flowchart of a single-stream *Chlamydia trachomatis* assay for the platform of FIG. 1A.

As illustrated in FIG. 1B, biological material extraction, such as DNA extraction, can be facilitated by charge-based interaction of biological components, such as nucleic acids, from the sample 11 with the magnetic beads 23 in the cartridge. The samples can be processed within the cartridge with the assistance of an automation instrument 30, which may be a USB-controlled rotary manipulator 30' as described below, that includes an actuator arm 31 that can move, for example, rotate, along path 32, and also includes a magnet 33 at an end of the actuator arm that can magnetically manipulate the beads 23 to move within the cartridge 11 as the actuator moves along path 32. As shown in FIG. 1B, when the lysate 11 is transferred into the sample inlet 29, of cartridge 20 at stage 103-1, it mixes with binding solution 21, in which magnetic beads 23 may be disposed, to form a sample lysate mixture. The binding buffer lowers the mixture's pH to acidic levels, for example, to a pH of 4 or 5. Because bead surface charge is positive at acidic pH (indicated as positively charged bead surface 23-1 at stage 103-1) and negative at alkaline pH (indicated as negatively charged bead surface 23-2 at stage 103-3), adsorption of DNA 12 from the sample 11 to the surface of the magnetic beads 23 is favored at stage 103-1, allowing for the separation of the DNA from other cellular debris 14, and elution of captured DNA, such as Ct genomic DNA, directly into a LAMP mixture.

The beads 23, having positively charged surface 23-1 to which DNA may be adhered, can be caused to move out of the binding buffer and into a wash buffer 25 as shown at stage 103-2. For example, a magnet, such as magnet 33 on the automation instrument, can be caused to move such as along path 32 via, for example, actuation motion of arm 31. Magnet 33 and magnetic beads 23 may each have a magnetic polarity such that they are either attracted to each other or repulsed from each other via a magnetic attractive or repulsive force between them. As a result of the motion of magnet 33 along path 32, the magnetic force can cause the magnetic beads 23 to move within volume 28 of the cartridge, and possibly. Accordingly, in an embodiment the magnetic beads 23 and magnet 33 can be magnetically attracted to one another via appropriate selection of magnetic properties of each. In an embodiment magnetic beads 23 may be magnetically repelled from one another via appropriate selection of magnetic properties of each.

The wash buffer may have a pH that is different than a pH of the binding buffer. For example, binding buffer 21 may have a pH of 4 and the wash buffer may have a pH of 5. Thus, with the wash buffer 25 being less acidic than the binding buffer, the surface 23-1 of magnetic beads 23 may be less positive than in the binding buffer.

The magnetic beads 23 that may have biological material 12, such as DNA, adhered to the surface 23-1 thereof may be caused to move out of the washing buffer 25 and into a LAMP mixture 27 at stage 103-3. For example, the magnetic beads 23 can be caused to move through volume 28 as magnet 33 moves along path 32. That is, after washing, the beads 23 may be transported to the LAMP mixture 27 for direct elution of DNA 12. The LAMP mixture may have a pH that is higher than a pH of the wash buffer 25 such that the magnetic particles attain a negative surface charge 23-2 for which biological material, such as DNA, adhesion is not favorable and causes release of the previously-adhered biological material. For example, the LAMP mixture may have a pH of 8.8, which favors release of bound DNA from the magnetic bead surface.

Incubation at 65° C. initiates isothermal DNA amplification. Thus, upon target amplification via LAMP at stage 103-3, color change from violet (as indicated by the shading at 103-5), to blue (as indicated by the shading at 103-7) is observed using a metal ion indicator dye. In other words, while not limited to any particular theory, it is believed that amplification of LAMP reaction product results in generation of pyrophosphates during synthesis, which chelates magnesium ion in solution and induces a color shift from violet to blue. Thus, as the magnetic particles are caused to move from the binding buffer 21 at stage 103-1 and to the LAMP reagent 27 at stage 103-3, for example, via an externally actuated permanent magnet 33 coupled to a rotary arm 31 of an automation instrument 30, such as a rotary manipulator/a servo motor, a single stream assay such as the single-stream *Chlamydia trachomatis* assay can be realized, as illustrated in the flow-chart of FIG. 1B.

A. Assembly

The cartridge 20 may be formed according to any method that results in a structure that provides the features described herein. In an embodiment, the assay described above can be realized on a cartridge 20, which may be a PMMA-based cartridge, and can be a single-use cartridge. In an embodiment, cartridge 20 may be fabricated as illustrated in FIG. 2A. The fabrication process shown in FIG. 2A includes (i) lamination at 201; (ii) patterning at 203, and (iii) assembly processes at 205.

Fabrication processes of the embodiments may provide a rapid turnaround time and may not require access to clean room facility. Generally, device fabrication can be achieved by lamination of a hydrophobic layer, such as a hydrophobic tape, to a hydrophilic substrate, such as the PMMA substrate, followed by patterning of the substrate with tape disposed thereon, which may be performed using a laser cutter. Such a method does not require any chemical modification of substrates. Accordingly, fabrication processes of embodiments are highly amenable to integration with a roll to roll fabrication process and are significantly different from clean room processes described by others.

In another embodiment of a fabrication process for at least upper and lower portions of the cartridge, a hydrophobic material can be deposited, for example, in combination with a patterned mask on a hydrophilic surface of a substrate, to form a pattern that includes such openings to the hydrophilic surface of the underlying substrate, such as the upper and lower portions of the cartridge as described above.

A-1. Lamination

In a lamination process 201, at 201-1 an upper cartridge portion 22 is provided by forming a first hydrophobic layer 22-2, such as PTFE tape, on a first substrate 22-1, such as a 0.5 mm thick layer of PMMA. At 201-3, a lower cartridge portion 26 can be provided by forming a second hydrophobic layer 26-2, such as PTFE tape, on a second substrate 26-1, such as a 0.75 mm layer of PMMA.

At 201-2, a spacer portion 24 can also be provided that includes a spacer frame 24-2 which may be a 1.5 mm layer of PMMA. A first adhesive layer 24-1, such as a pressure sensitive acrylic, can be formed on a first surface of the spacer frame. A second adhesive layer 24-2, such as a pressure sensitive acrylic, can be formed on a second surface of the spacer frame.

The adhesive layers 24-1 and 24-2 can be formed on the spacer portion in the first lamination process and then patterned while already formed on the spacer portion during a patterning process 203, or can be separately patterned and added onto the spacer frame during the assembly process 205.

Any or all of the upper cartridge portion, spacer portion and lower cartridge portion can be formed on one another via lamination in a roll-to-roll process.

A-2. Patterning

In a patterning process 203, a cartridge shape may be designed at 203-1, for example, utilizing computer-automated-design software. The cartridge may be designed to have any shape. For example, the upper cartridge portion 22, spacer portion 24 and lower cartridge portion 26 may be selected to have an outer radius, an inner radius and patterning between the outer and inner radius. The design of each of 22, 24 and 26 may be incorporated onto the laminated sections prepared at 201-1, 201-2, and 203-3 via patterning, such as by laser cutting, at step 203-2.

For example, with respect to upper cartridge portion 22, at least one of a plurality of first openings 22-1' can be formed through first hydrophobic layer 22-2 to form a pattern 22-2' of hydrophobic material with the openings 22-1' that exposes portions of the underlying substrate. The first openings 22-1' can be etched through the hydrophobic layer 22-1 using known etching techniques to form an etched pattern, and the portion of the first hydrophobic layer defined by the etched pattern can be removed from on the first substrate to reveal a hydrophilic surface of the first substrate through openings 22-1'. At least one of a plurality of second openings 26-1' can be formed through the second hydrophobic layer 26-2, for example via etching to form an etched pattern 26-2' of hydrophobic material with the openings 26-1', and a portion of the second hydrophobic layer defined by the etched pattern can be removed to expose a hydrophilic surface of the second substrate 26-1. For example, portions of the etched hydrophobic layer 26-2, which may be an etched PTFE tape layer, can be removed from the substrate 26-1 at 203-3. In an example, the openings can be formed by laser etching (i.e., laser cutting) through the second hydrophobic layer at 203-2. The substrate 24-2 and adhesive layers 24-1 and 24-2 can also be patterned into a spacer frame 24-1' which may define the volume 24-2' (see for example at FIG. 2B) of spacer portion 24. Additionally, a sample inlet 29 can be patterned through the upper cartridge portion. In an embodiment, the components of the cartridge, such as the upper portion 22, spacer portion 24 and lower portion 26, can be fabricated using at least one of hot embossing, blow molding, CNC milling and 3D printing.

3. Assembly

In a second lamination assembly process 205, the patterned upper cartridge portion 22, spacer portion 24 and lower cartridge portion 26 can be laminated together with the spacer 24 formed between the upper 22 and lower 26 cartridge portions. In an example, the first adhesive layer 24-1 can be formed between a first surface of the spacer frame 24-1' and the upper cartridge portion 22, such as at along outer perimeter surfaces of each of the spacer 24 and upper cartridge portion 22. The second adhesive layer 24-3 can be formed between a second surface of the spacer frame 24-1' and the bottom cartridge portion 26, such as at along outer perimeter surfaces of each of the spacer 24 and lower cartridge portion 26. As discussed previously, the adhesive layers can be added in the first lamination process 201 and then patterned at 203 while already formed on the spacer frame, or can be separately patterned (not shown) and added onto the spacer frame during the assembly process.

A volume 24-2' that is at least partially defined by sidewalls of the spacer frame 24-1', corresponds to the volume of channel 28 in FIG. 2B, which is formed upon assembly of the upper 22 and lower 26 cartridge portions to either side of the spacer portion 24 during the second lamination assembly process 205. The channel 28 can be configured, for example, as a result of the patterning process, to fluidically couple a sample inlet section and a sample analysis section of the cartridge.

During the assembly process or after assembly, the channel 28 can be at least partially filled with an isolating medium 19, such as an oil, as described below and shown in FIG. 2B. Additionally, at least one magnetic bead 23 can be provided to travel within the channel 28. At least one aqueous reagent pendant, such as a volume of binding buffer 21, wash buffer 25 and/or LAMP reagent 27 can also be added to the channel 28. The at least one pendant can be placed in the cartridge such that such that a portion thereof contacts one of the plurality of exposed hydrophilic surfaces of the first substrate, and/or another portion of the at least one pendant contacts one of the hydrophilic surfaces of the second substrate exposed by the at least one second opening of the second patterned hydrophobic layer. At least one biochemical reaction mixture can be included in the analysis section, wherein a portion of the at least one biochemical reaction mixture contacts another one of the exposed surface portions of the first substrate, and another portion of the at least one biochemical reaction mixture contacts the exposed surface of the second substrate.

The upper cartridge portion, spacer portion and lower cartridge portions can be laminated together and held together with the adhesive Sample Processing Cartridge Accordingly, in an embodiment, there is a sample processing cartridge that includes an upper cartridge portion 22, a lower cartridge portion 26 and a spacer 24 formed between the cartridge portions. The upper cartridge portion can include a first patterned hydrophobic layer 22-2' formed on a first substrate, and the lower cartridge portion can include a second patterned hydrophobic layer 26-2' formed on second substrate.

As shown in FIG. 2B, a channel 28' that is at least partially defined by sidewalls of the spacer's frame 24-1' and surfaces of upper portion 22 and lower portion 26, fluidically couples a sample inlet 29 section and a sample analysis section of the cartridge, and can be at least partially filled with an isolation medium 19. At least one magnetic bead 23 can be disposed in the channel 28 and is capable of being transported through the isolation medium 19 and from the inlet section to the sample analysis section via, for example, an external magnetic force. At least one volume of a liquid, such as at least one pendant of liquid that may comprise an aqueous reagent as discussed above, can be disposed in the channel 28. The at least one aqueous reagent pendant, such as binding buffer 21, wash buffer 25 and/or LAMP reagent 27, can be isolated from other portions of the channel and/or other ones of the plurality of aqueous reagent pendant by hydrophilic patterns formed in the upper cartridge portion, to which each of the aqueous reagents can anchor.

For example, as shown in FIGS. 2A-2B, the cartridge can include two functional layers, such as an upper substrate layer 22-1 of upper cartridge portion 22 and a lower substrate layer 26-1 of lower cartridge portion 26, separated by a spacer frame 24-1' of spacer portion 24. The upper layer can be laminated with PTFE sealing tape to generate a smooth hydrophobic surface. Although PTFE is a common hydrophobic sealant available as a tape, materials other than or in addition to PTFE can be used for forming hydrophobic surfaces that define the channel. For example, any fluorocarbon-treated material with adhesive properties can be applied to the upper and lower layers. Sample is introduced at the sample inlet 29, which, as shown in FIG. 2B, is defined by an opening that extends through the first substrate 24-1. The sample inlet can instead be defined by an opening that extends through other portions of the cartridge and can include appropriate valving to prevent leakage of the isolation medium from out of the channel.

The hydrophilic patterns of the upper cartridge portion can include a plurality of first openings 22-1' that extend through the first hydrophobic layer and expose a corresponding plurality of hydrophilic surfaces of the first substrate 22-1. Additionally, hydrophilic patterns of the lower cartridge portion can include at least one, and for example, a plurality, of openings 26-1' that extend through the second hydrophobic layer and expose a corresponding plurality of hydrophilic surfaces of the first substrate 22-1. For example, hydrophilic PMMA patterns, such as spots, can be revealed on the upper cartridge portion 22, lower cartridge portion 24 or both the upper and lower cartridge portions, by etching a pattern through the hydrophobic layers 22-2 and 26-2, with, for example, a $CO_2$ laser cutter, and then peeling away the portions of the hydrophobic layers defined by the etched pattern. In other words, a pattern of hydrophilic surfaces of the PMMA substrates can be exposed by laser-assisted etching of portions of the hydrophobic PTFE tape layers to expose the PMMA surface below. While the upper cartridge portion, lower cartridge portion and/or frame portion can be made of PMMA, the embodiments are not so limited. For example, the upper cartridge portion, lower cartridge portion and/or frame portion can be selected from any material with (i) sufficient chemical inertness so as to not react with the sample, isolation material or reagents, (ii) that has a thermal stability at an incubation temperature of 65° C., (iii) has hydrophilic surfaces, and (iv) is compatible with an adhesives.

By patterning the surfaces of upper portion 22 and lower portion 26, anchoring of at least one, or multiple aqueous reagent pendants is possible, and each can be sealed in an isolation medium 19, such as a fluorinated oil. In an embodiment, the isolation medium material includes a continuous oil phase. As used herein, the term continuous oil phase refers to an oil which is not compartmentalized such that a molecule of the oil phase at one location in the continuous oil phase can travel to any other location in the oil without trespassing into another phase. The isolation medium can prevent evaporation of the at least one liquid pendant and can also isolate each of the plurality of liquid pendant, such as the aqueous reagent. Therefore, the least one liquid pendant, which can be a binding buffer, a wash buffer or LAMP reagent, can be disposed in the channel 28 and isolated by the isolation medium 19. Additionally, a portion of the at least one liquid pendant may contact one of the plurality of exposed hydrophilic surfaces of the upper cartridge portion, such as a surface of the first substrate, and/or may contact one of the plurality of exposed hydrophilic surfaces of the lower cartridge portion, such as a surface of the second substrate.

In an embodiment, the at least one aqueous reagent pendant comprises a binding buffer 21 disposed in an input chamber portion stage 103-1 of the channel, a wash buffer 25 disposed in a wash portion stage 103-2 between the binding buffer and an amplification portion stage 103-3, which may include a LAMP mixture 27. The binding buffer, the wash buffer and the LAMP mixture may each be separated from one another by a volume of the isolation medium 19. As discussed above, DNA will bind to a surface of the magnetic beads or release from the surface depending on the pH of the environment surrounding the magnetic bead. Accordingly, a pH of the binding buffer may be lower in magnitude (i.e., more acidic) than a pH of the wash buffer.

In order to promote isolation of the aqueous reagent and limit its evaporation, while also allowing transport of the magnetic particles and biological agents adsorbed to a surface of the magnetic particles, the isolation medium 19 can permeable to the magnetic beads but not to the at least one aqueous reagent. For example, FLUORINERT® FC-40 (available from Sigma-Aldrich, St. Luis, Mo.) can be selected as the isolation medium. Other oils with comparable viscosity to FLUORINERT® FC-40 can also be used, particularly those with a boiling temperature sufficiently greater than the incubation temperature of about 65° C. While a liquid isolation medium is preferable, in an embodiment other materials or devices can be used to allow transport of the magnetic particles while also isolating the aqueous reagent.

Figure 2C:
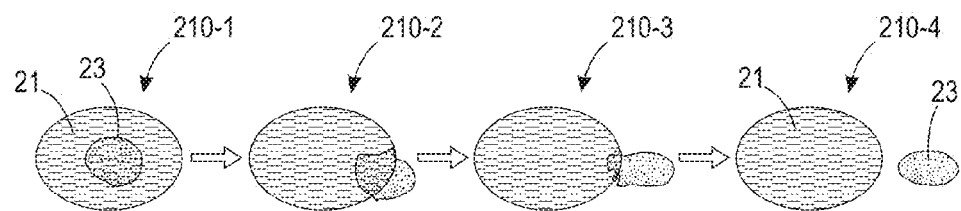
FIG. 2C is a photograph of a magnetic plug dissociation sequence.

The magnetic beads 23 can be transported along the hydrophilic layer of the second substrate of the lower cartridge portion 26, through the isolation medium 19 and through the at least one aqueous reagent, for example, the binding buffer 21, wash buffer 25 and/or LAMP reagent 27. For example, as shown in the magnetic bead plug dissociation sequence of FIG. 2C, efficient splitting of magnetic beads from reagents can be achieved. At 210-1 in FIG. 2C, magnetic beads 23 are in an aqueous reagent, such as binding buffer 21. As a magnet (not visible) such as magnet 33 is moved to a position such that a magnetic force exists between the magnet 33 and magnetic beads 23 such that the magnetic beads are sufficiently attracted to magnet 33 or sufficiently repelled from magnet 33, the magnetic beads 23 are caused to move, for example out of the aqueous reagent as in 210-2. As the magnet is moved even more, more of the magnetic beads 23 move out of the reagent as in 210-3 until finally at 210-4, most if not all of the magnetic beads, with, for example, biological material of interest on a surface of the beads, are moved completely out of the reagent, such as binding buffer 21. Thus embodiments can be configured such that the beads can freely traverse through reagents and through the isolation fluid on a continuous PTFE surface to an analysis section within a cartridge 20, where the beads, as well as any biological agent of interest attached to the surface of the beads, can be introduced to a biological reaction mixture such as the LAMP mixture as described above.

To isolate the at least one reagent pendant, the hydrophobic layer such as the PTFE can be patterned to reveal a hydrophilic surface of the lower substrate, such as the PMMA layer, as shown in FIG. 2B. For example, a PTFE surface disposed on a lower layer may contact the at least one reagent and can facilitate transportation of magnetic beads across reagents, wash buffers and to biological reaction mixtures. While not limited to any particular theory, it is believed that the PTFE surface on the lower layer compresses reagent droplets, forming cylindrical columns of aqueous reagents and isolated in a continuous fluorinated oil phase.

Accordingly, the lower cartridge portion can also include a hydrophilic pattern that has at least one second opening that extends through the second hydrophobic layer and exposes a corresponding hydrophilic surface of the second substrate. At least one reagent, such as a biochemical reaction mixture, can be disposed in the analysis section of the cartridge and isolated by a isolation medium and/or the hydrophilic pattern of the upper and/or lower cartridge portions. For example, a portion of the at least one biochemical reaction mixture can contact another one of the plurality of exposed hydrophilic surface of the first substrate, and another portion of the at least one biochemical reaction mixture contacts the exposed hydrophilic surface of the second substrate.

Automated Sample Processing System

Figure 3:
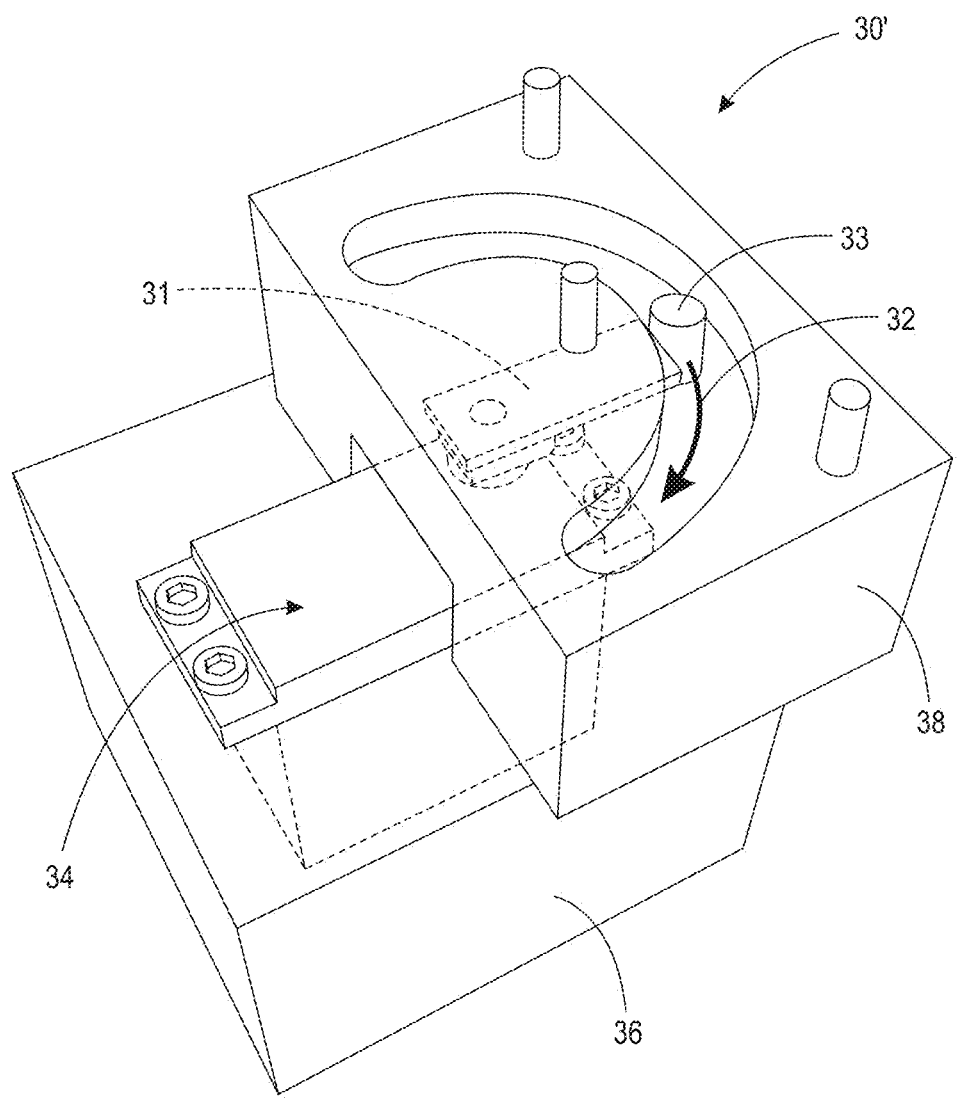
FIG. 3 is a perspective view of an automation instrument of an embodiment.
Figure 4:
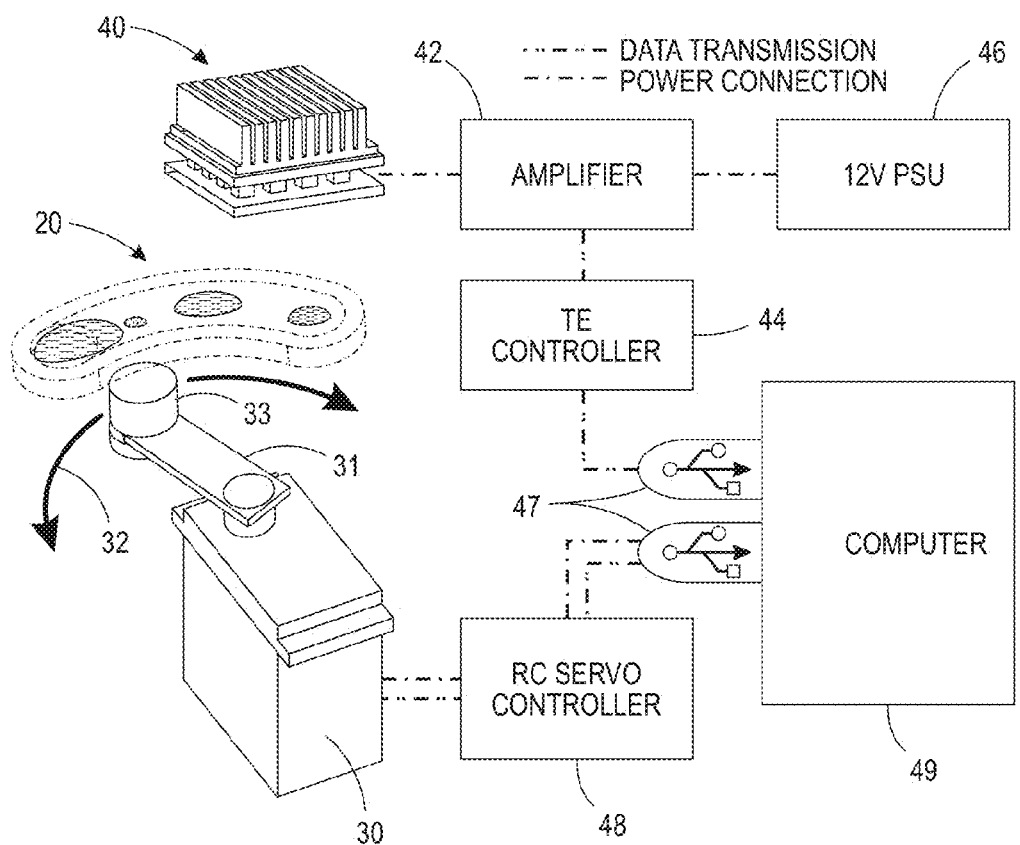
FIG. 4 provides a schematic overview of an automated sample processing system.

Automation can be achieved with instrumentation shown and described in FIGS. 3-4. Accordingly, in an embodiment there is a sample processing system that can be an automated sample processing system. The system can include the cartridge 20 of FIG. 2B, and an automated instrument such as an actuating cartridge stand 30' shown in FIG. 3. The actuating cartridge stand 30 can include a housing 36, a actuator motor 34 disposed within the body, a manipulator arm 31 controlled by the motor, and a magnet 33 at the end of the arm 31. The actuator disposed in a cartridge stand 30 may include a platform 38 on which the cartridge 20 can be placed. The manipulator arm 31 can be configured such that an end thereof, such as the end on which magnet 33 is disposed, can traverse a path 32. The actuator, with magnet on the manipulator arm, can be configured such that it can apply a magnetically induced force, via magnet 33, against the at least one magnetic bead 23 disposed in a cartridge, such as the magnetic bead 23 in the cartridge of FIG. 2B, when the magnet is brought to a predetermined proximity of the bead as shown in FIG. 4

As shown in FIG. 4, the system can also include a host device to power the automated instrument, such as an actuator. Rotary actuation is an economical alternative to linear translation and well-suited to point-of-care applications. Accordingly, the actuator can be powered by a host device, such as a USB-powered servo motor controller, and magnet 33, such as a permanent magnet, may be mounted on the actuator's rotor arm. In another embodiment, the magnet may be an electromagnet which can also be USB-powered.

The sample processing cartridge 20 of the embodiments can be curved, such that a sample inlet that is offset by a radial distance from a sample analysis section of the cartridge where a biochemical reaction mixture is stored. In an example, the sample inlet opening and the analysis section are offset by an angle about 70° as shown in FIG. 2A. In an embodiment, the cartridge can be designed as large as necessary such that the channel is formed along a curved path that the external rotary arm can follow up to a physical limit of 360° C. The arc length between each of the at least one reagent, for example aqueous reagent, should be selected as about 5 mm to provide robust magnetic bead transport.

The servomotor controller 48 can be powered by a host device 49 which can be a USB host device. The host device 49 can be a desktop computer, a laptop computer, a tablet computer or a smart phone for enabling programmable movement of the actuator, arm and magnet. A computer program, for example one written for use with LabVIEW software (available from National Instruments, Corp., Austin, Tex.), can be executed by the host device 49, such as a computer to send signals to a controller 48, which then translates the signals for controlling the actuator. A sequence of angular positions along path 32 can be included in such a computer program to guide the magnet 33 on the rotor arm 31 to cause the magnets in the cartridge to be transported across various locations of the cartridge, such as the at least one plurality of reagents and isolation materials in the cartridge.

The system can also include additional electronics for data transmission and appropriate power connection such as a power supply unit 46 and a power amplifier 42, and additional components, such as a TE controller 44 and a heater unit 40 for dispelling excess heat from the system. Additionally, although cartridges 20 of some embodiments allow for visual detection of nucleic acid targets based on color changes upon exposing sample DNA to a biochemical reaction mixture as described above, the system can include an integrated colorimetric signal acquisition and processing system. For example, the colorimetric signal acquisition and processing system can be included on a single mobile device serving as the host device 49.

EXAMPLES

Assay sensitivity was evaluated in a bench top process. FIGS. 5A and 5B show the colorimetric readout sensitivity at 10 genomic copies/reaction and assay sensitivity at 10 CFU/reaction. FIG. 5A shows sensitivity results obtained with samples of *Chlamydia trachomatis* cell culture dilutions were verified using 2% agarose gel electrophoresis. Successful LAMP amplicons are elongated as a growing chain of repeating sequences, which is observed on the gel image as a set of growing ladders. As shown in FIG. 5A, amplification is observed for up to $10^1$ CFU/reaction. FIG. 5B shows sensitivity results for colorimetric readout.

Assay was performed in 25 µL reaction volume. Magenta/violet (magnified box on right hand side) indicates negative amplification while light blue (magnified box on left hand side) indicates positive amplification. Color changes were observed up to copies per reaction. Gel electrophoresis verification confirmed successful amplification up to the same input concentration (data not shown).

Figure 6:
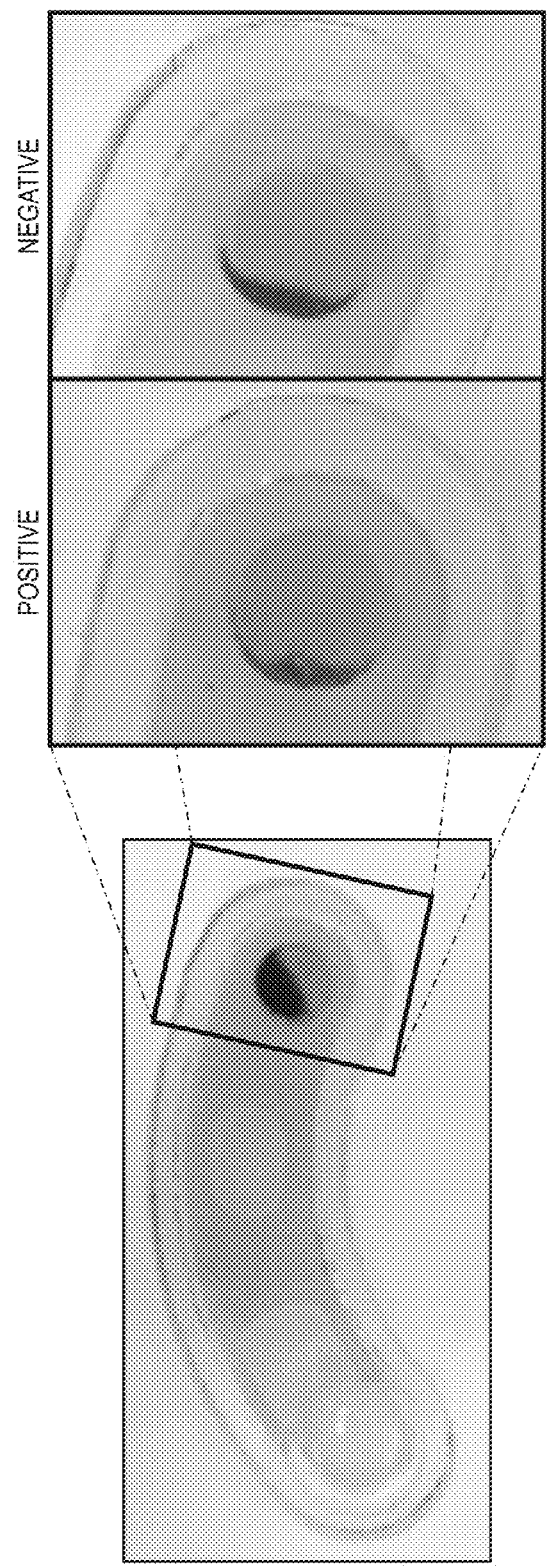
FIG. 6 shows a processed sample in a cartridge with exemplary positive and negative results.

A sample processing cartridge system of an embodiment described above was used to test samples of self-collected vaginal swabs from a high-risk population for Ct transmission and acquisition. As shown in the post reaction cartridge in FIG. 6, magnetic beads were cleared to the periphery of the reaction in the sample analysis section of the cartridge to reveal the color of the completed reaction at the end of LAMP reaction.

The swabs were initially expressed in 1× Tris-EDTA buffer and tested with GEN-PROBE® APTIMA COMBO2® assay (available from Gen-Probe, Inc., San Diego, Calif.) for comparative reference. Six remaining aliquots of identified samples were blinded and tested on a sample processing cartridge system of an embodiment of the platform described herein (i.e., on chip testing). The comparison table in Table 1 below shows colorimetric readout correctly identifying infected samples as compared to the APTIMA COMBO2® conventional system. Infected samples (2, 4 and 6) turned blue while negative samples (1, 3 and 5) remained violet or magenta, as shown in the photograph Accordingly, one benefit of the embodiments described herein includes an integrated Ct detection platform at the point-of-care.

TABLE 1

|  | Sample ID | | | | | |
| --- | --- | --- | --- | --- | --- | --- |
|  | 1 | 2 | 3 | 4 | 5 | 6 |
| Prototype Result | − | + | − | + | − | + |
| GenProbe Result | − | + | − | + | − | + |

While the invention has been illustrated respect to one or more implementations, alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function.

Furthermore, to the extent that the terms "including", "includes", "having", "has", "with", or variants thereof are used in either the detailed description and the claims, such terms are intended to be inclusive in a manner similar to the term "comprising." As used herein, the phrase "one or more of", for example, A, B, and C means any of the following: either A, B, or C alone; or combinations of two, such as A and B, B and C, and A and C; or combinations of three A, B and C.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sample processing cartridge, comprising:
 an upper cartridge portion comprising a first substrate and a first hydrophobic layer formed on a surface of the first substrate;
 a lower cartridge portion comprising a second substrate and a second hydrophobic layer formed on a surface of the second substrate;
 a spacer frame formed between the upper portion and the lower portion;
 a sample inlet section comprising a sample inlet;
 a sample analysis section offset by a distance from the sample inlet section;
 a channel that (a) is at least partially defined by sidewalls of the spacer frame, (b) is at least partially filled with an isolation medium, and (c) fluidically couples the sample inlet section and the sample analysis section;
 at least one magnetic bead disposed in the channel;
 a plurality of first openings that extend through the first hydrophobic layer and expose a corresponding plurality of hydrophilic surfaces of the first substrate;
 at least one second opening that extends through the second hydrophobic layer and exposes a corresponding hydrophilic surface of the second substrate;
 at least one aqueous reagent pendant disposed in the channel and isolated by the isolation medium, wherein a portion of the at least one aqueous reagent pendant contacts one of the plurality of exposed hydrophilic surfaces of the first substrate; and
 at least one biochemical reaction mixture disposed in the analysis section and isolated by the isolation medium, wherein a portion of the at least one biochemical reaction mixture contacts another one of the plurality of exposed hydrophilic surfaces of the first substrate, and another portion of the at least one biochemical reaction mixture contacts the exposed hydrophilic surface of the second substrate,
 wherein the isolation medium is permeable to the at least one magnetic bead but not to the at least one aqueous reagent pendant.

2. The sample processing cartridge of claim 1, wherein the isolation medium comprises a liquid.

3. The sample processing cartridge of claim 1, wherein the isolation medium comprises a fluorinated oil.

4. The sample processing cartridge of claim 1, wherein the at least one aqueous reagent pendant comprises a binding buffer disposed in an input chamber portion of the channel and a wash buffer disposed between the binding buffer and the biochemical reaction mixture, and wherein the binding buffer and the wash buffer are separated by a volume of the isolation medium.

5. The sample processing cartridge of claim 4, wherein a pH of the binding buffer is lower in magnitude than a pH of the wash buffer.

6. The sample processing cartridge of claim 3, wherein the sample inlet comprises an opening that extends through the first substrate.

7. The sample processing cartridge of claim 1, wherein the first hydrophobic layer, the second hydrophobic layer, or both the first hydrophobic layer and the second hydrophobic layer comprise PTFE tape.

8. The sample processing cartridge of claim 4, wherein the at least one biochemical mixture comprises a pH that is higher than a pH of the wash buffer mixture.

9. The sample processing cartridge of claim 1, further comprising a first adhesive layer formed between a first surface of the spacer frame and the upper cartridge portion, and a second adhesive layer formed between a second surface of the spacer frame and the bottom cartridge portion.

* * * * *